US008486424B1

(12) United States Patent
Stojkoski

(10) Patent No.: US 8,486,424 B1
(45) Date of Patent: Jul. 16, 2013

(54) METHOD OF PREPARING A SKIN TREATMENT COMPOSITION

(76) Inventor: Radmila Stojkoski, Sterling Heights, MI (US)

( * ) Notice: Subject to any disclaimer, the term of this patent is extended or adjusted under 35 U.S.C. 154(b) by 794 days.

(21) Appl. No.: 11/857,152

(22) Filed: Sep. 18, 2007

(51) Int. Cl.
| | |
|---|---|
| *A61K 8/02* | (2006.01) |
| *A61K 33/42* | (2006.01) |
| *A61K 33/24* | (2006.01) |
| *A01N 59/26* | (2006.01) |
| *A01N 59/16* | (2006.01) |

(52) U.S. Cl.
USPC .......... 424/401; 424/603; 424/604; 424/606; 424/653

(58) Field of Classification Search
USPC .................. 424/63, 604, 401, 603, 606, 653
See application file for complete search history.

(56) References Cited

U.S. PATENT DOCUMENTS

| | | | | | |
|---|---|---|---|---|---|
| 4,297,374 | A | * | 10/1981 | Wess | 514/777 |
| 5,017,367 | A | * | 5/1991 | Stojkoski | 424/63 |

FOREIGN PATENT DOCUMENTS

DE    2600388    7/1977

OTHER PUBLICATIONS

Safe Handling of Milk and Dairy Products (see topic Butter: pp. 3 and 4, published by Clemson University 2002-2007) and publication date tracking record by Internet Archive Wayback Machine for http://hgic.clemson.edu/factsheets/hgic3510.htm.*
Types of Edible Solid Fats: topic Butter: p. 1, lines 3-7, retrieved online via www.recipetips.com.*
Experiments and Techniques in Organic Chemistry (1992), Chapter 2: Separation and Purification Techniques, section 2.1 Filtration, p. 40.*
Mikhail Tombak (obtained from the article: Can We Live 150 Years, Published in 2004, via online http://books.google.com/books, p. 107, lines 3-7).*
Mikhail Tombak (Book: Can We Live 150 Years: First English Edition (2003), p. 107, lines 3-14).*
Book; Ash, Michael and Irene, "A Formulary of Cosmetic Cosmetic Preparations", Chemical Publishing Co., New York, New York; Chapter VI, Creams and Lotions, pp. 248-249; Chapter XI, Miscellaneous, pp. 396-399, 422-423, (Jul. 27, 1981).
Book; Gregory, Thomas C., "Uses and Applications of Chemicals and Related Materials", Reinhold Publishing Corporation, New York, New York; p. 109, (Jun. 2, 1944).
Book; Harry, Ralph G., "The Principles and Practice of Modern Cosmetics", vol. Two, "Cosmetic Materials", 1963 Chemical Publishing Co., Inc., New York, New York; pp. 456-459, (Mar. 12, 1963).
Book; "Pharmaceutical Formulas", P.F. vol. I., Twelfth Edition, 1953 The Chemist and Druggest, London, W.C.2; pp. 650-651, (May 3, 1954).
Book; "Pharmaceutical Formulas", P.F. vol. II, Tenth Edition, 1946 The Chemist and Druggest, London, W.C.2, pp. 444-453, 554-555, (Jan. 21, 1947).
Catalog; "Puritan's Pride", 1983, "Honey Almond Deep Cleansing Facial Scrub", (year: 1983).

* cited by examiner

*Primary Examiner* — Mina Haghighatian
*Assistant Examiner* — Helen Chui
(74) *Attorney, Agent, or Firm* — Reising Ethington PC

(57) ABSTRACT

One embodiment includes a method including boiling unsalted butter over low heat until it appears golden to form purified butter; cooling the purified butter by removing it from the heat; straining or filtering the purified butter; refrigerating the purified butter for at least 24 hours; thoroughly blending together the elements of an organic carrier medium, wherein the organic carrier medium comprises the purified butter, olive oil, and honey; adding distilled water to the blended organic carrier medium; mixing the distilled water and the blended organic carrier medium at high speed; and adding at least one of sodium acid pyrophosphate, cornstarch, bismuth subnitrate, salicylic acid, or alkali metal salicylates, and mixing.

13 Claims, No Drawings

METHOD OF PREPARING A SKIN TREATMENT COMPOSITION

TECHNICAL FIELD

The field to which the disclosure generally relates includes a method of preparing a composition for the cleaning and treatment of skin.

BACKGROUND

Various topical skin care preparations are known in the art. It would be desirable to have a method of preparing a skin treatment composition which is gentle enough for topical application on delicate or sensitive skin such as those found on the face.

SUMMARY OF EXEMPLARY EMBODIMENTS OF THE INVENTION

One embodiment includes a method including heating butter to form purified butter; cooling the purified butter by removing it from the heat; straining or filtering the purified butter; refrigerating the purified butter; forming an organic carrier medium by blending at least one of the purified butter, olive oil, honey or mixtures thereof; adding distilled water to the blended organic carrier medium; mixing the distilled water and the blended organic carrier medium; and adding at least one of sodium acid pyrophosphate, cornstarch, bismuth subnitrate, salicylic acid, or alkali metal salicylates, and mixing.

Other exemplary embodiments of the invention will become apparent from the detailed description of exemplary embodiments provided hereinafter. It should be understood that the detailed description and specific examples, while indicating the exemplary embodiments of the invention, are intended for purposes of illustration only and are not intended to limit the scope of the claimed invention.

DETAILED DESCRIPTION OF EXEMPLARY EMBODIMENTS

The following description of the embodiment(s) is merely exemplary in nature and is in no way intended to limit the invention, its application, or uses.

In the method of preparing a skin treatment composition according to one embodiment of the invention, various thickeners and moisturizers are admixed with the active ingredient sodium acid pyrophosphate to produce a highly effective topical skin care composition which can be used as a cleaner, moisturizer and healing agent for minor skin irritations. In one embodiment the method produces a topical skin care composition consisting essentially of:

(a) an organic carrier medium;

(b) an organic adsorption agent present in a ratio of about 0.25 to about 1 part thickening agent to about 1 part organic carrier;

(c) sodium acid pyrophosphate present in a ratio of about 0.001 to about 0.1 part sodium acid pyrophosphate to about 1 part organic carrier; and (d) water present in a ratio of about 0.001 to about 1 part water per 1 part organic carrier in an emulsified state with the organic carrier base.

As can be readily appreciated, in various embodiments of the method, the topical skin care composition produced can be formulated as a creme, salve, paste or the like. As expressed below, parts, unless otherwise indicated refers to parts by weight. In one embodiment, the proportions are adjusted such that the admixture of the above-listed ingredients forms a creme or salve. In such formulations, the organic carrier medium and water are adjusted such that the ratio of carrier to water is an amount ranging from about 5 to about 25 parts carrier per each part water.

In one embodiment, the carrier medium may be composed of purified butter and a liquid food-grade oil. In addition to the ability of these components to maintain water and the sodium acid pyrophosphate in a dispersed and emulsified state, these components act as a moisturizer when applied to the skin. In one embodiment, the carrier is composed of purified butter, olive oil and honey. In one embodiment, the carrier is composed of about 40 to about 75 percent by weight purified butter based on the total weight of the carrier, and about 24 percent by weight to about 55 percent by weight of olive oil based on the total weight of the carrier. Additionally, trace amounts of honey can be added to the carrier. In one embodiment, honey is added in an amount of about 0.05 percent by weight to about 1 percent by weight based on the total weight of the carrier.

The carrier medium is emulsified with water. The water is added in an amount of about 0.001 to about 1 parts water per one part of the carrier medium. The water and organic carrier medium are blended at high speed to form an emulsion. In one embodiment, the water may be distilled . . . .

The skin treatment composition also contains an organic adsorptive or thickening agent. This material is generally a powdered, granulated, or particulate solid capable of thickening the carrier base. The organic thickening agent may be capable of adsorbing or absorbing excess oils which may be present on the skin. Additionally, the particulate thickener may provide a "matte-like", natural appearance if the skin treatment composition is to be applied to the skin for prolonged periods. It has been found that a starch-based agent is most advantageously employed herein. In one embodiment, the starch-based agent may comprise commercially-available food-grade cornstarch.

In one embodiment sodium acid pyrophosphate employed is admixed into the carrier medium as a granulated or powdered solid material. The amount of sodium acid pyrophosphate may be added in a ratio of about 0.001 parts to about 0.1 parts sodium acid pyrophosphate per 1 part carrier.

Sodium acid pyrophosphate is commercially available from numerous chemical supply houses. Another suitable source of sodium acid pyrophosphate is found in a type of baking powder manufactured under the trade name OETKER. This baking powder contains leavening agents consisting essentially of a mixture of sodium bicarbonate and sodium acid pyrophosphate. The presence of sodium bicarbonate in the mixture when OETKER baking powder is employed as the sodium acid pyrophosphate source in no way impairs the performance of the skin treatment composition of the present invention.

The presence of sodium acid pyrophosphate in the composition of the present invention may markedly reduce the number of blemishes attributable to bacteria present on the skin and in pores. Without being bound to any theory, it is believed that sodium acid pyrophosphate acts as a bacteriocidal or bacteriostatic agent; killing or inactivating various microorganisms present on the skin surface. The sodium acid pyrophosphate may have an astringent effect without the harshness of conventional astringents.

The topical skin care composition produced by the method of one embodiment can also contain optional ingredients such as perfumes, coloring agents and the like. The perfumes may be selected from any suitable commercially available fragrance. The coloring agent, where used, is employed to leave a pleasing skin tone when the topical skin care composition is applied. On such coloring agent is cocoa powder present in the skin care composition in a ratio of about 0.001 to about 1.0 part cocoa powder per 1 part carrier base. One embodiment includes adding the perfume or coloring agent to the blended organic carrier medium and mixing.

In various embodiments, other optional compounds may be added to the skin treatment composition. In one embodiment, bismuth subnitrate is added in a ratio of about 0.001 to about 0.1 part bismuth subnitrate to 1 part carrier base. Bismuth subnitrate may exhibit therapeutic properties as a healing agent for minor epidermal skin irritations.

In a method according to one embodiment, a variety of suitable preservatives may be added to the topical skin care composition. In one embodiment, at least one of salicylic acid, alkali metal salicylates and mixtures thereof exhibits preservative qualities when added to the skin treatment composition. The preservative may be present in a ratio of about 0.001 to about 0.1 part preservative to about 1 part carrier base. It has also been found, quite unexpectedly, that salicylic acid or the salicylate salts thereof are effective to forestall and minimize wrinkles when added to the skin treatment composition of the present invention in the amounts listed above.

In preparing the present composition, the components of the carrier, water, sodium acid pyrophosphate, adsorbent, and any optional ingredients are admixed in a given order at standard temperature and pressure.

First, the ingredient of purified butter is prepared. The method includes boiling unsalted butter over low heat until it appears golden to form purified butter. The use of low heat may minimize the risk of burning or overly browning the butter. Further, the boiling may drive off water from the raw butter. The purified butter is cooled by removing it from the heat. The purified butter is then strained or filtered to remove solids. The purified butter is refrigerated until ready for use. The purified butter may be refrigerated for at least 24 hours before further use. The purified butter may be strained or filtered using any suitable strain or filter, for example a sieve or a cheese-cloth lined strainer. The use of purified butter may enhance the shelf life of the final composition.

In one embodiment the organic components of the carrier are thoroughly blended. Water is added to the blended organic components and mixed at high speed to create an organic-aqueous emulsion. Mixing may proceed for approximately 15 minutes. It is to be understood that the consistency of the emulsion will vary given the mixing speed and mixing time employed. In one embodiment the emulsion may be extremely fine and have highly dispersed water. After the emulsion is formed, the sodium acid pyrophosphate, cornstarch, and any optional ingredients are added thereto. This admixture is then mixed to provide a homogenous mixture of appropriate consistency. It is to be understood that variances in the ratio of water and dry ingredients to carrier base will yield skin treatment compositions of different consistencies varying from lotion to ointment to cream to paste as desired.

Where the additional ingredients are employed, the skin treatment composition of the present invention is prepared by blending the healing agents such as bismuth subnitrate, the preservatives such as salicylic acid and the coloring agents into the composition together with the sodium acid pyrophosphate. It should be noted that the optional ingredients need not all be utilized at one time. Rather, any optional ingredient, alone, or any combination thereof, can be used.

Without being bound to any theory, it is believed that the presence of sodium acid pyrophosphate in the skin treatment composition imparts unique astringent and cleansing properties to the skin treatment composition of the present invention. It is believed that the presence of sodium acid pyrophosphate acts in concert with the other compounds in the composition of the present invention to promote the dislodgement and removal of dirt, unwanted old makeup and dead epidermal cells from both the surface of the skin and within clogged pores without damaging existing healthy skin tissue. The astringent properties of the sodium acid pyrophosphate when employed in admixture with the components of the skin treatment composition may further assist in thorough skin cleansing. Those properties combined with the moisturizing properties of the skin treatment composition may permit the skin treatment composition to provide thorough skin cleansing and moisturizing as well as preventing reoccurrence of such skin problems as blackheads for a substantial period after use.

In one embodiment, the skin treatment composition may be employed as a cleanser or a moisturizer. The skin treatment composition may be applied for daytime or nighttime use. The skin treatment composition may be used for example to effectuate moisturizing the skin, or cleansing the skin, or both. It is intended that in most instances, the skin treatment composition when applied to the skin is not to be washed off or otherwise removed.

In one preferred embodiment, the skin treatment composition has the consistency of a cosmetic cream. The composition is applied to the skin and massaged into the skin. Most of the composition will be absorbed. Thereafter, the skin may be buffed with a suitable soft fabric, such as for example an applicator for loose powder.

The above description of embodiments of the invention is merely exemplary in nature and, thus, variations thereof are not to be regarded as a departure from the spirit and scope of the invention.

What is claimed is:

1. A method of making a skin treatment composition suitable for topical application comprising:
   heating butter to form purified butter;
   cooling the purified butter by removing it from the heat;
   straining or filtering the purified butter;
   refrigerating the purified butter prior to blending or mixing the purified butter with any other ingredient;
   forming an organic carrier by blending at least one of the purified butter, olive oil, honey or mixtures thereof;
   adding distilled water to the blended organic carrier medium;
   mixing the distilled water and the blended organic carrier medium; and
   adding at least one of sodium acid pyrophosphate, cornstarch, bismuth subnitrate, salicylic acid or mixtures thereof, and mixing.

2. A method as set forth in claim 1 wherein the butter is unsalted and is heated by boiling the butter over low heat until it appears golden.

3. A method as set forth in claim 1 wherein the cornstarch is present in a ratio of about 0.25 to about 1 part cornstarch to about 1 part carrier medium.

4. A method as set forth in claim 1 wherein the sodium acid pyrophosphate is present in a ratio of about 0.001 to about 0.1 part sodium acid pyrophosphate to about 1 part carrier medium.

5. A method as set forth in claim 1 wherein the salicylic acid is present in a ratio of about 0.001 to about 0.1 part salicylic acid to about 1 part carrier medium.

6. A method as set forth in claim 1 wherein the distilled water is present in a ratio of about 0.001 to about 1 part water to about 1 part carrier medium.

7. A method as set forth in claim 1 wherein the bismuth subnitrate is present in a ratio of about 0.001 to about 0.1 part bismuth subnitrate to about 1 part carrier medium.

8. A method as set forth in claim 1 further comprising adding a coloring agent to the blended organic carrier medium and mixing.

9. A method as set forth in claim 1 further comprising adding perfume to the blended organic carrier medium and mixing.

10. A method as set forth in claim 1 wherein the distilled water is present in an amount equal to the olive oil and the purified butter.

11. A method as set forth in claim 1 wherein the mixing the distilled water and the blended organic carrier medium at high speed is performed for about 15 minutes.

12. A method as set forth in claim 1 wherein the purified butter is refrigerated for at least 24 hours.

13. A method as set forth in claim 1 wherein the carrier medium consists of (a) the purified butter present in an amount of about 0.40 to about 0.75 parts per about 1 part carrier medium; (b) the olive oil present in an amount of about 0.24 to about 0.55 parts per about 1 part carrier medium; and (c) the honey present in an amount of about 0.005 to about 0.01 parts per about 1 part carrier medium.

\* \* \* \* \*